United States Patent [19]

Waldenburg

[11] Patent Number: 5,496,284
[45] Date of Patent: Mar. 5, 1996

[54] DUAL-CHAMBER SYRINGE & METHOD

[76] Inventor: Ottfried Waldenburg, P.O. Box 548, Sells, Ariz. 85634

[21] Appl. No.: 312,878

[22] Filed: Sep. 27, 1994

[51] Int. Cl.⁶ ........................................... A61M 5/19
[52] U.S. Cl. ........................................ 604/191; 604/89
[58] Field of Search ........................... 604/191, 187, 604/89, 91, 92, 246, 218, 181, 183, 184

[56] References Cited

U.S. PATENT DOCUMENTS

| | | |
|---|---|---|
| 212,046 | 2/1879 | Palmer . |
| 213,978 | 4/1879 | Dibble . |
| 368,627 | 8/1887 | Threlfall . |
| 553,234 | 1/1896 | Finot . |
| 936,205 | 10/1909 | Woodruff . |
| 1,950,137 | 3/1934 | Dowe ............................. 604/191 |
| 3,749,084 | 7/1973 | Cucchiara ..................... 604/191 X |
| 4,655,747 | 4/1987 | Allen, Jr. ........................... 604/89 |
| 4,834,714 | 5/1989 | Lascar et al. ................ 604/191 X |
| 5,078,691 | 1/1992 | Hamacher . |
| 5,143,211 | 9/1992 | Miczka et al. . |

FOREIGN PATENT DOCUMENTS 554894  4/1931  Germany .

*Primary Examiner*—John D. Yasko
*Attorney, Agent, or Firm*—John J. Connors; Connors & Associates

[57] ABSTRACT

A dual-chamber syringe has a plunger within an inner delivery chamber in fluid communication with an ejection port. The deliver chamber is formed within a tubular element axially slidable within a tubular guide. The tubular guide and the syringe outer barrel form an outer reservoir chamber. The outer reservoir chamber is sealed from the delivery chamber while the tubular element is in a first position within the guide. Upon withdrawal of the plunger, frictional contact imparted by the plunger seal causes the tubular element to slide away from sealing engagement with the barrel into a second position within the guide. In the second position of the tubular element, a fluid passageway is opened from the reservoir to the delivery chamber allowing fluid to be drawn into the delivery chamber. A porous seal between the plunger rod and barrel allows air into the reservoir during transfer of fluid to the delivery chamber. Pressing the plunger inward first moves the tubular element from the second position back to the first position to close the fluid passageway and then expels fluid from the delivery chamber through the ejection port.

12 Claims, 3 Drawing Sheets

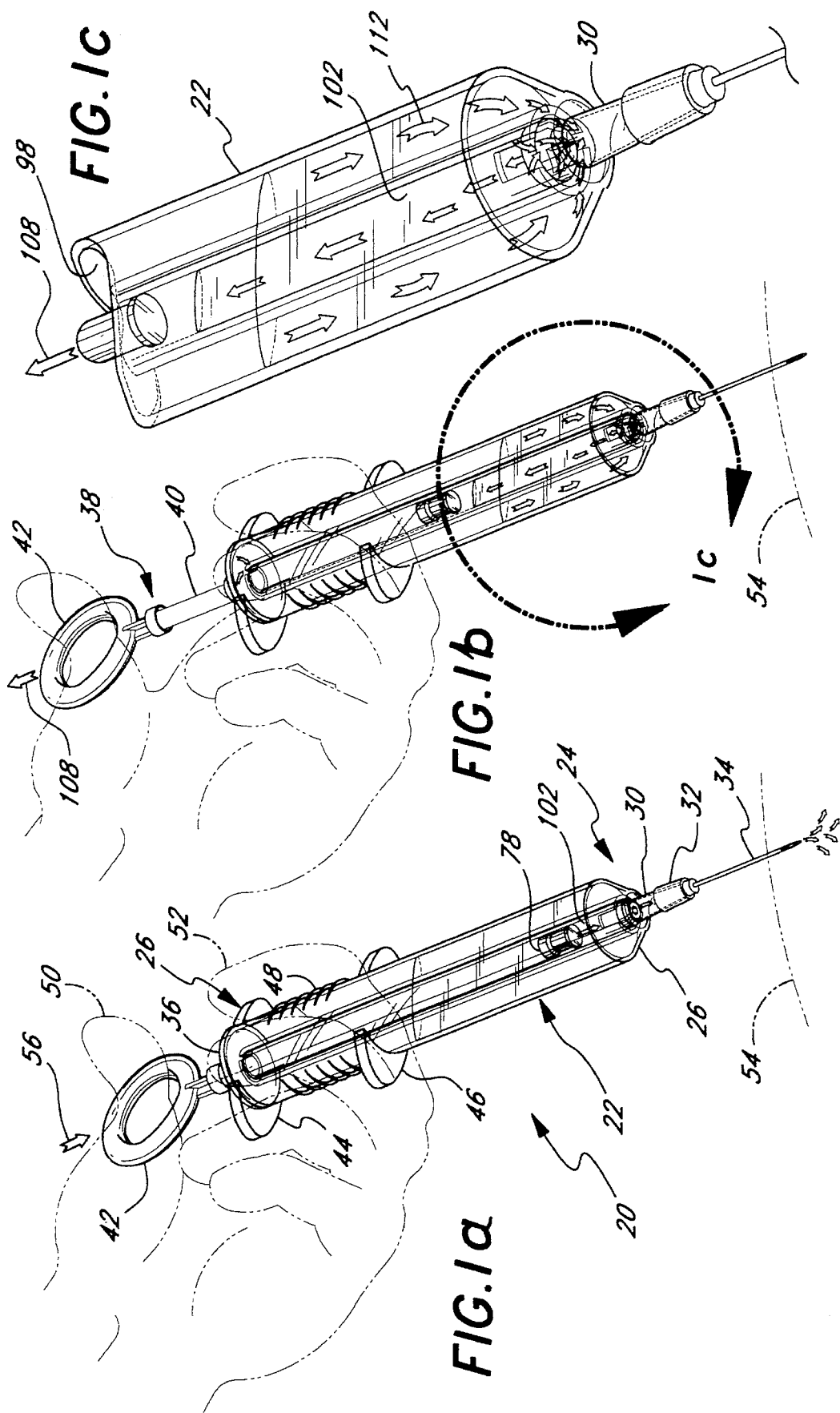

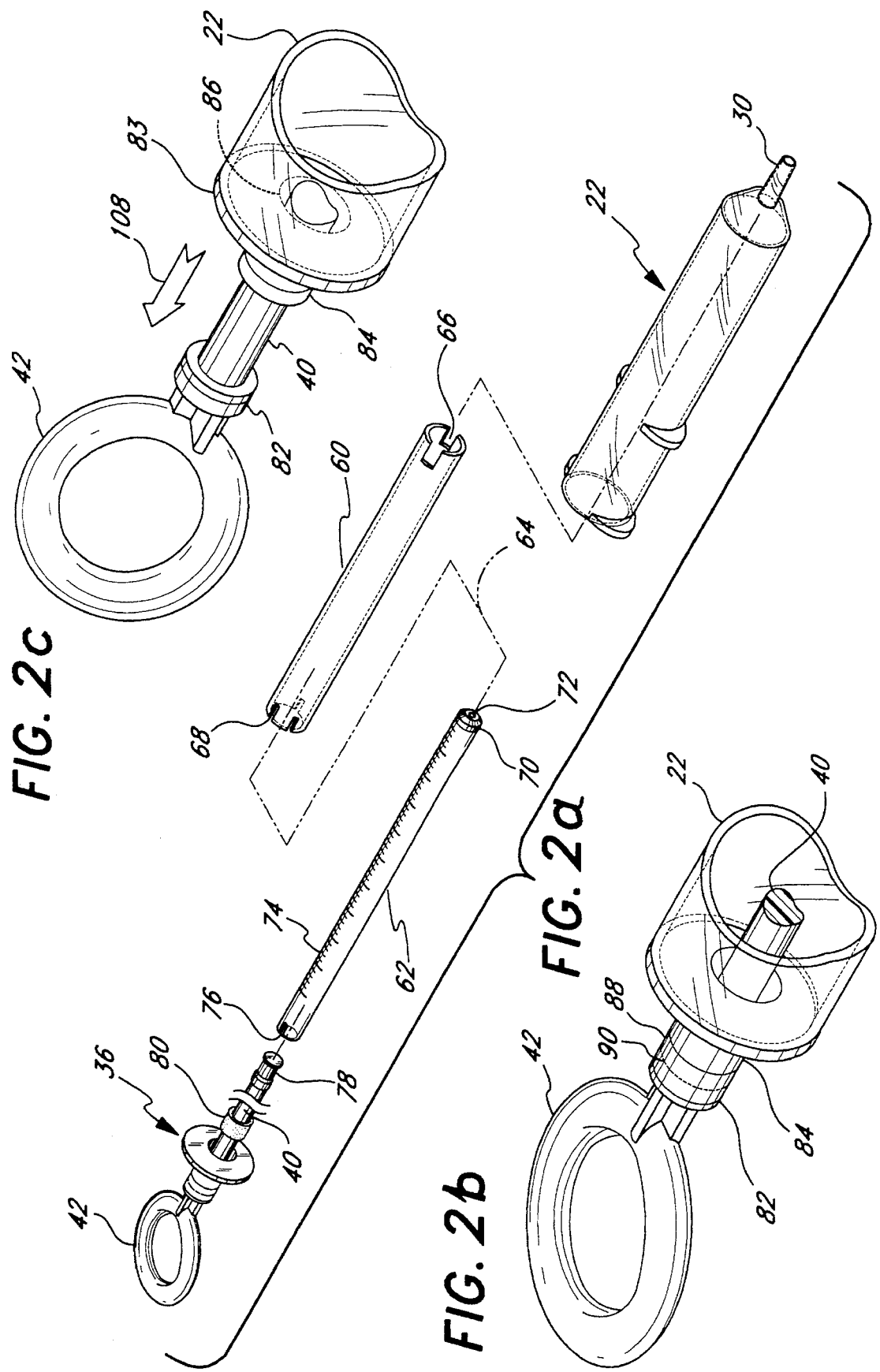

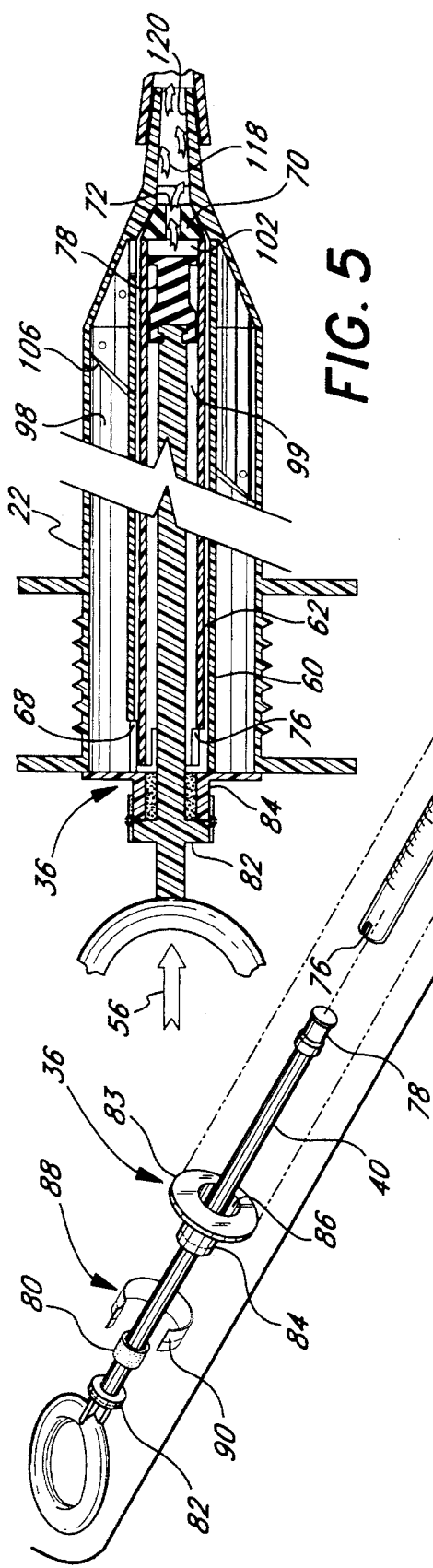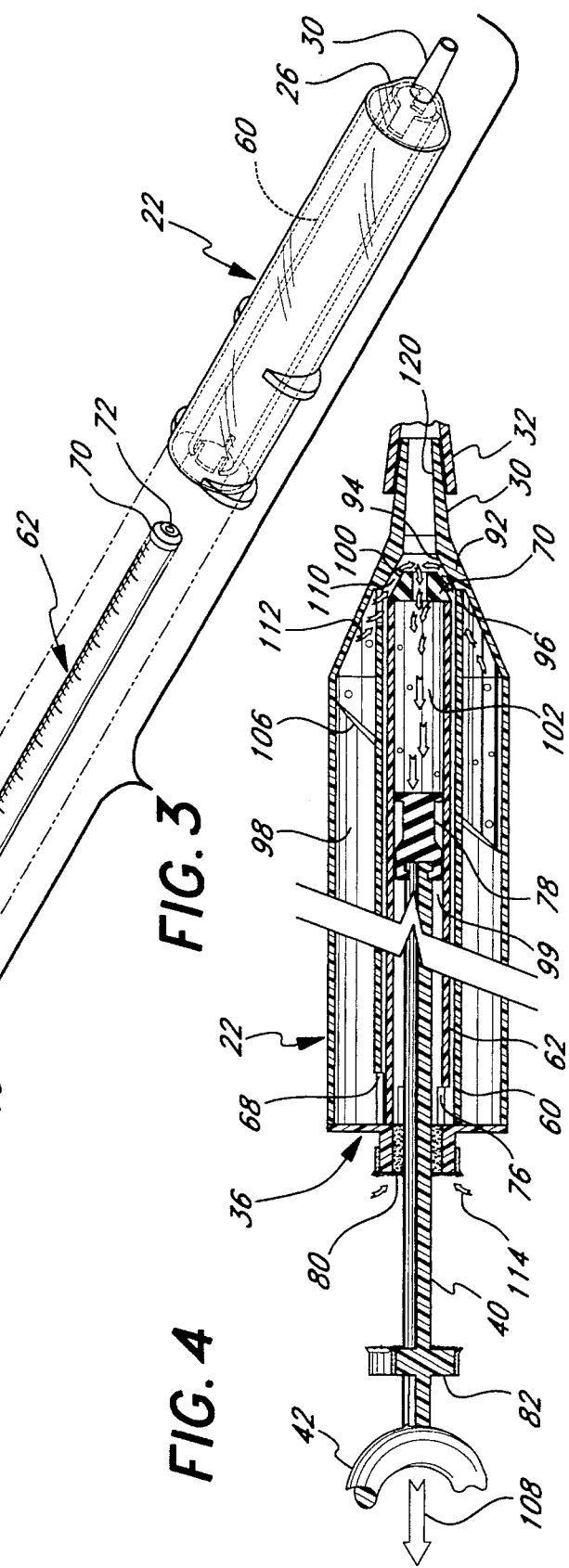

5,496,284

DUAL-CHAMBER SYRINGE & METHOD

BACKGROUND OF THE INVENTION

1. Field of the Invention

This invention relates to an improved syringe and, more particularly, to a dual-chambered syringe having a fluid reservoir accessible to a delivery chamber upon axial displacement of a plunger.

2. Background Discussion

In many medical procedures there is a need for locally anesthetizing a large region subject to an operation or other treatment. Local administration of anesthetic may require several distinct injections in the affected area, or injection of a first volume of anesthetic at a relatively shallow depth followed by one or more further injections after advancing the hypodermic needle deeper into the tissue of the patient, or both. This successive delivery of anesthetic to varying tissue depths ensures a complete and measured numbing of all of the nerve endings in the treated region.

When delivering a large quantity of any fluid using a syringe, such as in the successive, varying depth injection method, the syringe must have a large capacity, or must be withdrawn intermittently and refilled. Large syringes are cumbersome, and it is often difficult to meter small quantities with them as the barrel has a large cross-section. Thus, even a small movement of the plunger correlates to a large fluid displacement. Moreover, the smaller the diameter of the syringe, the less pressure is required to deliver the injection, and consequently, less pain. Withdrawal of the syringe from an injection site for refilling and subsequent re-injection is inconvenient and increases the chance of infection and trauma to the patient.

There have been efforts in the prior art to provide a dual-chamber syringe for storing a volume of fluid in a reservoir to be transferred into a delivery chamber, or visa versa. Typically, the fluid is ejected from the delivery chamber through a nozzle by a plunger. There are various motivations for providing dual-chamber syringes, including simply increasing the syringe capacity, providing a sterile self-contained single-use syringe, and mixing two components prior to injection, for example. Many of the known devices, however, require the injection nozzle to be plugged prior to transferring fluid between the reservoir and the delivery chamber. In other known devices, one chamber is placed in communication with another only upon relative rotation of the chamber barrels.

One dual-chamber syringe is shown in U.S. Pat. No. 553,234 issued to Finot. This syringe includes a rotatable inner chamber for selectively communicating the inner chamber with either the injection nozzle or the reservoir. Despite the benefit of a larger carrying capacity, the syringe must be manipulated with two hands to transfer fluid between chambers. Further, the syringe of Finot was not designed for successive, varying depth injections which are best accomplished rapidly and with minimum lateral movement.

Despite numerous previous dual-chamber syringe designs, all share the drawback of requiring a two-handed operation to transfer fluid between the internal chambers. There is thus a need for a dual-chamber syringe particularly suited for successive, varying depth injections which can be actuated with one hand.

SUMMARY OF THE INVENTION

The syringe of this invention has several features, no single one of which is solely responsible for its desirable attributes. Without limiting the scope of this invention as expressed by the claims which follow, its more prominent features will now be discussed briefly. After considering this discussion, and particularly after reading the section entitled, "DETAILED DESCRIPTION OF THE PREFERRED EMBODIMENT," one will understand how the features of this invention provide its benefits, which include one-handed operation; convenience of use; larger capacity; successive, varying depth injection of anesthetic; ease of introduction of medication into dense tissue; better control of quantity of anesthetic used, thereby avoiding unnecessary tissue swelling; filtration of air introduced into syringe; the use of a single needle to give multiple injections without the need to remove the needle from the body of the patient; reduction of pain during injection because smaller diameter needles may be used; and elimination of vials holding medication, thereby reducing of likelihood contamination.

The first feature of the medical syringe of this invention is that it includes a plunger having at one end a resilient seal, and a barrel having a central longitudinal axis and a pair of opposed ends. The plunger has at an end remote from the end with the resilient seal thereon a thumb ring, and the barrel has at least one external finger rest. The barrel has at one end an ejection port and at the other end an opening. Preferably, the opening in the barrel has a porous seal which surrounds the plunger. This porous seal allows air to enter the barrel yet inhibits the flow of liquid from the chamber. The ejection port and opening are aligned with each other and disposed along the longitudinal axis.

The second feature is outer and inner telescopic tubular elements seated inside the barrel to be coaxial with the longitudinal axis. The outer tubular element is mounted in a stationary position while disposed in the barrel and the inner tubular element is movable axially within the outer tubular element. The outer tubular element and barrel form a chamber which holds a reservoir of liquid. The outer tubular element has a fluid passageway therein that allows the liquid to flow from the chamber into the inner tubular element. The inner tubular element has an end nearby the injection port with a seal thereon that has an orifice therein. This inner tubular element receives the end of the plunger with the resilient seal thereon.

The third feature is that the resilient seal fits snug within the inner tubular element to grip the inner tubular element. In response to axial movement of the plunger, the inner tubular element is moved between a first and second positions. In the first position, the seal with the orifice therein seals the injection port as the plunger is moved towards the injection port, preventing liquid in the chamber from passing into the inner tubular element and forcing any liquid in the inner tubular element through the orifice and out the injection port. In the second position, the seal with the orifice therein is moved to a retracted position away from the injection port, allowing liquid to flow from the chamber through the passageway and through the orifice into the inner tubular member.

The fourth feature is that the plunger is initially in a forward position that forces the seal with the orifice therein into engagement with the injection port to seal this port. Preferably, there is a safety seal on the plunger which is broken by movement of the plunger into a retracted position, pulling the seal with the orifice therein away from the injection port. This thereby initially fills the inner tubular element with liquid from the chamber. Preferably, the barrel and inner and outer tubular elements are made of a transparent or translucent material.

This invention also includes a method of giving an injection of an anesthetic into the body of a patient. This method includes the steps of (a) providing a syringe with a reservoir that contains the anesthetic and a delivery channel which receives a plunger which when moved in one direction places the channel in communication with the reservoir and in another direction discontinues the communication and ejects anesthetic from the channel, (b) initially introducing the anesthetic using the syringe into the body of the patient, and (c) introducing a second dosage of the anesthetic by moving the plunger in the one direction to place the reservoir into communication with the channel and refill the channel with anesthetic and then moving the plunger in the other direction to discontinue the communication and eject anesthetic from the channel.

In this method only one hand is used to manipulate the syringe.

DESCRIPTION OF THE DRAWING

The preferred embodiment of this invention, illustrating all its features, will now be discussed in detail. This embodiment depicts the novel and non-obvious syringe and method of this invention as shown in the accompanying drawing, which is for illustrative purposes only. This drawing includes the following figures (FIGS.), with like numerals indicating like parts:

FIG. 1a is a perspective view of a dual-chamber syringe of the present invention during delivery of fluid to an injection site through a needle.

FIG. 1b is a perspective view of the dual-chamber syringe during transfer of a fluid from an internal reservoir to a delivery chamber.

FIG. 1c is an enlarged perspective view of a distal end of the syringe in FIG. 1b showing fluid flow from the reservoir into the delivery chamber.

FIG. 2a is an exploded, perspective view of the dual-chamber syringe showing the components of the syringe.

FIG. 2b is an enlarged perspective view of a proximal end of the dual-chamber syringe prior to rupture of a safety seal;

FIG. 2c is an enlarged perspective view similar to FIG. 2b after the safety seal has been ruptured;

FIG. 3 is another exploded, perspective view of the syringe showing the components of the syringe.

FIG. 4 is a cross-sectional view of the syringe during transfer of fluid from an internal reservoir to a delivery chamber.

FIG. 5 is a cross-sectional view of the syringe during delivery of a fluid through an ejection port.

DETAILED DESCRIPTION OF THE PREFERRED EMBODIMENT

As shown in FIG. 1a, a dual-chamber medical syringe 20 includes an outer tubular barrel 22 including a distal end 24 and a proximal end 26. The distal end 24 includes a tapered section 28 leading to a stem 30 for receiving a hub 32 of a needle 34. Those skilled in the art will understand that the stem 30 is of a generally standard type in the medical industry, and various needles and the like will be readily received thereon.

The proximal end 26 of the barrel 22 is covered by an end cap 36 having an aperture 86 (FIG. 3) for receiving a plunger 38. The plunger 38 includes a plunger rod 40, as seen in FIG. 1b, and a thumb ring 42 on its proximal end. The barrel 22 further includes a first pair of outwardly extending finger rests 44 adjacent to the end cap 36 and a second pair of outwardly extending finger rests 46 proximally disposed with respect to the first pair. Additionally, a series of external circumferential grip ribs 48 are formed on the barrel 22 between the finger rests 44, 46.

The syringe 20 is thus configured to allow a medical technician to insert a thumb 50 through the thumb ring 42 while gripping the barrel 22 with the index and middle fingers 52 in the general location of the ribs 48. The syringe 20 exhibits both finger rests 44 and 46 to allow an operator to displace the thumb ring 42, and associated plunger rod 40, in either axial direction with respect to the barrel 22. FIG. 1a shows the needle 34 after having pierced an injection site 54. Movement of the plunger 38 in the direction of arrow 56 relative to the barrel 22 forces fluid out of the needle 34, as shown by arrows 58. Advantageously, this one-handed operation facilitates rapid and steady, successive, varying depth injections, as will be more fully explained below.

Looking now at FIG. 2a, the cylindrical barrel 22 is sized to receive a channel member or tubular guide 60 which, in turn, receives a tubular element 62. When assembled, the three tubular elements 22, 60 and 62 fit concentrically within one another along a common longitudinal axis 64. The tubular guide 60 is slightly longer than the tubular element 62. When assembled, as shown in FIG. 4, the proximal end of the guide member 60 contacts the end cap 36, and distal end abuts the tapered section 28. The tubular element 62, on the other hand, is free to slide axially within the guide member 60 a short distance, the reason for which will be explained further below.

The tubular guide 60 includes a pair of diametrically opposed axial slots 66 in the distal end and a plurality of axial slots 68 in the proximal end. The tubular element 62 is fitted with an elastomeric, plunger-like seal 70 on its distal end having an orifice 72 therethrough. A large portion of the tubular element 62 is marked with a series of volumetric graduations 74. A breather slot 76 is formed in the distal end of the tubular element 62.

The plunger 38, as shown exploded in FIG. 3, includes a resilient fluid seal 78 attached to the distal end. A porous sleeve or seal 80 fits snugly around the plunger rod 40 intermediate the seal 78 and a stop ring 82. The end cap 36 is defined by a flat disk portion 83 sized to cover the proximal end of the barrel 22 and a circular flange 84 extending in a proximal direction. A central throughbore 86 of the end cap 36 receives the plunger rod 40. The throughbore 86 is sized to fit snugly over the porous seal 80. As seen in FIG. 4, the porous seal 80 fills the annular space between the piston rod 40 and the throughbore 86 of the end cap 36.

A safety seal 88 is provided for packaging and safe transport of the syringe 20 while carrying liquid. More particularly, the plunger 38 assumes a fully depressed position during transport with the stop ring 82 juxtaposed against the circular flange 84, as shown in FIG. 2b. The safety seal 88, which may be, for example, one-sided tape, is adhered around the junction of the stop ring 82 and flange 84. A perforated circle 90 is provided around the mid-portion of the safety seal 88. Upon first twisting and then moving of the plunger 38 in the direction of arrow 91 in FIG. 2c, the perforated circle 90 is ruptured allowing the syringe 20 to operate as desired. As indicated, the rupture of the perforated circle 90 may be facilitated by rotating the thumb ring 42 and integral stop ring 82 relative to the barrel 22.

Now looking at FIG. 4 and 5, the outer barrel 22 includes a thickened region 92 adjacent the stem 30. The thickened region 92 has an inner tapered surface 94. At the proximal end of the region 92, a circular ledge 96 forms a contact and centering ring for the tubular guide 60. The annular space between the tubular guide 60 and the barrel 22 defines an outer fluid chamber or reservoir 98. The reservoir 98 serves as the primary receptacle for storing liquid medication, such as an anesthetic, or other fluid to be injected. However, due to the presence of the axial slots 68 and 76, fluid can freely pass between the reservoir 98 and a proximal portion 99 of the interior of the tubular element 62, although the syringe 20 is intended to function best with the majority of fluid remaining in the reservoir.

The resilient seal 70 on the distal end of the tubular element 62 has a forward taper 100 configured to seal against the tapered surface 94 of the barrel 22. As mentioned above, the tubular element 62 has an axial length such that it may move a short distance between the tapered surface 94 and the end cap 36 and within the confines of the guide 60.

The resilient seal 78 divides the inner volume of the tubular element 62 into a distal portion or delivery chamber 102 and the proximal portion 99. Thus, the delivery chamber 102 is in fluid communication with an ejection port 120 in the stem 30 when the tubular element 62 is in a distal position and the seal 70 is engaged with the tapered surface 94 as shown in FIG. 5. In this position, the seal 70 prevents fluid from passing between the reservoir 98 and the delivery chamber 102. The tubular element 62 may be displaced proximally into a second position shown in FIG. 4 wherein the seal 70 is disengaged from the tapered surface 94. In this second position, fluid may travel through a passageway 110 between the tapered surfaces 94 and 100. Thus, only when the tubular element 62 is slid into the second position can fluid travel from the reservoir 98 to the delivery chamber 102.

Assembly

The present syringe 20 is designed to be filled with anesthetic or other fluid prior to final assembly and then transport to a hospital or medical facility for use. More particularly, the syringe 20 is assembled by first inserting the tubular guide 60 into the barrel 22 until the distal end contacts and seats on the circular ledge 96. Next, the tubular element 62 is slid within the guide 60. After assembling the porous seal 80 and end cap 36 over the stem 40, the plunger 38 is inserted into the tubular element 62, with resilient seal 78 being first placed into the tubular element. With the seal 70 of the element 62 pressed against the tapered surface 94, anesthetic or other fluid 106 is added to the reservoir 98 between the guide 60 and barrel 22. The disk portion 83 of the end cap 36 is then bonded to the proximal rim of the barrel 22. The means for bonding the cap 36 to the barrel 22 may be adhesion, heat seal, ultrasonic welding or other similar expedient. Finally, the plunger 38 is fully depressed so that the stop ring 82 comes into contact with the flange 84, whereupon the safety seal 88 is secured around the two components with the perforated circle 90 lined up in the junction plane.

The syringe 20 is then sealed from external contamination by the end cap 36, safety seal 88 and contact between seal 70 and tapered surface 94. A protective cap (not shown) may be attached over the stem 30 to prevent contamination in the ejection port 120.

Operation

In order to use the syringe 20, the safety seal 88 is first ruptured at the perforated circle 90 by a twisting motion of the thumb ring 42 relative to the barrel 22, as seen in FIG. 2c. At this point, fluid 106 remains within the reservoir 98 by the contact between the seal 70 and tapered surface 94. Proximal movement of the plunger 38 as seen by arrow 108 creates friction between the resilient seal 78 and the inner surface of the tubular element 62. This friction causes the tubular element 62 to be displaced in a proximal direction, opening up the fluid passageway 110 between the seal 70 and tapered surface 94. After the tubular element 62 contacts the end cap 36, further movement of the plunger 38 creates a suction or reduced pressure in the delivery chamber 102. This suction pulls fluid 106 into the delivery chamber 102 from the reservoir 98. The fluid flow, as shown by arrows 112, passes through the axial slots 66, the fluid passageway 110 and orifice 72. During proximal movement of the plunger 38, air is introduced into the barrel 22 through the porous seal 80, as shown by arrows 114 in FIG. 4. The frictional surface contact with the flange 84 maintains the position of the porous seal 80 while allowing the plunger rod 40 to slide relative thereto.

When the delivery chamber 102 is filled, the medical technician bleeds any air therein and expels anesthetic through the ejection port 120 until the proper volume remains, as indicated by the graduation markings 74. In order to view fluid against the graduated markings 74, the barrel 22, tubular guide 60 and tubular element 62 are formed of transparent or translucent materials. After advancement of the needle 34 a first depth into the injection site 54, anesthetic is expelled though the ejection port 120 by distal movement of the plunger 38 via the thumb ring 42, as shown by movement arrow 56 in FIGS. 1a and 5. Initial distal movement of the plunger seal 78 urges the tubular element 62, and more specifically the seal 70, into engagement with the tapered surface 94 of the barrel 22. This closes off the fluid passageway 110 between the reservoir 98 and the delivery chamber 102. Further movement of the plunger 38 thus forces fluid from the delivery chamber 102 until the resilient seal 78 bottoms out against the inner surface of the seal 70.

After a first infusion of anesthetic at the first depth of the needle 34, the syringe 20 is advanced to position the needle at a second depth. At this point, the plunger 38 is again withdrawn relative to the barrel 22 via the thumb ring 42 and finger rest 46. After the frictional contact of the resilient seal 78 pulls the tubular element 62 against the end cap 36, and upon further proximal movement of the plunger 38, a negative pressure develops within the delivery chamber 102. Due to the proximal movement of the tubular element 62, the fluid passageway 110 is once again opened for anesthetic to flow along the path of arrows 112 in FIG. 4 through the orifice 72 and into the delivery chamber 102. In this manner the syringe 20 is once again primed and ready to deliver another infusion of anesthetic at the second needle depth.

This process can be repeated at successive depths until the injection site is sufficiently numbed, or until the anesthetic in the reservoir 98 is exhausted. The entire sequence of infusion-advance-prime-infusion can easily be accomplished with the thumb and fingers of only one hand. Furthermore, the priming and expulsion of fluid from the delivery chamber 102 is done by simply advancing and retracting the plunger 38 along the axis of the syringe 20.

Another benefit of the present syringe 20 is the large capacity of the reservoir 98 in combination with the relatively small force required to infuse fluid into the patient. More particularly, the inner diameter of the tubular element 62 is preferably between 1.0 and 1.5 cm. This small size enables the operator to generate a large pressure within the delivery chamber 102 with the application of only small forces on the thumb ring 42. At the same time, the barrel 22 may have an inner diameter of between 2 and 3 times the diameter of the tubular element 62, resulting in a large fluid storage capacity available to the delivery chamber 102. Conversely, the small diameter of the tubular element 62 also enables the operator to generate a large negative pressure in the delivery chamber 102 making it easy to prime the syringe 20 for another injection. In other words, it is easy to suck fluid into the delivery chamber 102. This helps reduce fatigue to the hands of the operator during a large number of repetitive injections.

The initial priming of the syringe 20 is preferably done external to the injection site 54. The protective cap (not shown) over the stem 30 seals the ejection port 120 to enable the plunger 38 to pull fluid into the deliver chamber 102 from the reservoir 98, rather than air in through the ejection port. After the needle 34 has been buried in the injection site 54, the small size of the needle orifice provides sufficient resistance to entry into the needle 34 of relatively viscous bodily fluids. The negative pressure required to pull fluid 106 into the delivery chamber 102 is primarily related to the resistance of air passage through the porous seal 80. Thus, the seal 80 is designed to exhibit less resistance to air passage than the resistance of the needle orifice to bodily fluids.

SCOPE OF THE INVENTION

The above presents a description of the best mode contemplated of carrying out the present invention, and of the manner and process of making and using it, in such full, clear, concise, and exact terms as to enable any person skilled in the art to which it pertains to make and use this invention. This invention is, however, susceptible to modifications and alternate constructions from that discussed above which are fully equivalent. For example, the outside of the syringe may be marked to indicate the amount of fluid injected into a patient; the reservoir may be divided into separate compartments, each holding one component of a two component medication system; and the reservoir may be charged with a gas to create positive pressure within the reservoir, eliminating the filter/seal. Consequently, it is not the intention to limit this invention to the particular embodiment disclosed. On the contrary, the intention is to cover all modifications and alternate constructions coming within the spirit and scope of the invention as generally expressed by the following claims, which particularly point out and distinctly claim the subject matter of the invention:

I claim:

1. A medical syringe, including a plunger having at one end a resilient seal, a barrel having a central longitudinal axis and a pair of opposed ends, said barrel having at one end an ejection port and at the other end an opening, said ejection port and opening being aligned with each other and disposed along the longitudinal axis, outer and inner telescopic tubular elements seated inside the barrel to be coaxial with said longitudinal axis, the outer tubular element being mounted in a stationary position while disposed in the barrel and the inner tubular element being movable axially within the outer tubular element, said outer tubular element and barrel forming a chamber holding a reservoir of liquid, with the outer tubular element having a fluid passageway therein that allows the liquid to flow from the chamber into the inner tubular element, and the inner tubular element having an end nearby the injection port with a seal thereon that has an orifice therein, said inner tubular element receiving the end of the plunger with the resilient seal thereon, said resilient seal fitting snug within the inner tubular element to grip said inner tubular element and, in response to axial movement of the plunger, to move the inner tubular element between a first position where said seal with the orifice therein seals the injection port as the plunger is moved towards said injection port, preventing liquid in the chamber from passing into the inner tubular element and forcing any liquid in the inner tubular element through the orifice and out the injection port, and a second position where said seal with the orifice therein is moved to a retracted position away from the injection port, allowing liquid to flow from the chamber through the passageway and through the orifice into the inner tubular member.

2. The medical syringe of claim 1 where the opening in the barrel has a porous seal which surrounds the plunger, said porous seal allowing air to enter the barrel yet inhibits the flow of liquid from the chamber.

3. The medical syringe of claim 1 where the plunger is initially in a forward position that forces the seal with the orifice therein into engagement with the injection port to seal this port, and there is a safety seal on the plunger which is broken by movement of the plunger into a retracted position, pulling the seal with the orifice therein away from the injection port, to thereby initially fill the inner tubular element with liquid from the chamber.

4. The medical syringe of claim 1 where the plunger has at an end remote from the end with the resilient seal thereon a thumb ring, and the barrel has at least one external finger rest.

5. The medical syringe of claim 1 where the barrel and inner and outer tubular elements are made of a transparent or translucent material.

6. A medical syringe, including a plunger having at one end a resilient seal, a barrel having a central longitudinal axis and a pair of opposed ends, said barrel having at one end an ejection port and at the other end an opening, said ejection port and opening being aligned with each other and disposed along the longitudinal axis, outer and inner telescopic tubular elements seated inside the barrel to be coaxial with said longitudinal axis, the outer tubular element being mounted in a stationary position while disposed in the barrel and the inner tubular element being movable axially within the outer tubular element, said outer tubular element and barrel forming a chamber holding a reservoir of liquid, with the outer tubular element having a fluid passageway therein that allows the liquid to flow from the chamber into the inner tubular element, said opening in the barrel having a porous seal which surrounds the plunger, said porous seal allowing air to enter the barrel yet inhibits the flow of liquid from the chamber, the inner tubular element having an end nearby the injection port with a seal thereon that has an orifice therein, said inner tubular element receiving the end of the plunger with the resilient seal thereon, said resilient seal fitting snug within the inner tubular element to grip said inner tubular element and, in response to axial movement of the plunger, to move the inner tubular element between a first position where said seal with the orifice therein seals the injection port as the plunger is moved towards said injection port, preventing liquid in the chamber from passing into the inner tubular element and forcing any liquid in the inner tubular element through the orifice and out the injection port, and a second position where said seal with the orifice therein is moved to a retracted position away from the injection port, allowing liquid to flow from the chamber through the passageway and through the orifice into the inner tubular member, the plunger being initially in a forward position that forces the seal with the orifice therein into engagement with the injection port to seal this port, and a safety seal on the plunger which is broken by movement of the plunger into a retracted position, pulling the seal with the orifice therein away from the injection port, to thereby initially fill the inner tubular element with liquid from the chamber.

7. The medical syringe of claim 6 where the plunger has at an end remote from the end with the resilient seal thereon a thumb ring, and the barrel has at least one external finger rest.

8. The medical syringe of claim 6 where the barrel and inner and outer tubular elements are made of a transparent or translucent material.

9. A medical syringe, including a barrel with an ejection port at one end, an opening at the other end, and an internal partition member extending lengthwise between the opening and ejection port to provide a channel running between the ejection port and the opening and a chamber holding a reservoir of liquid, a moveable tubular element seated within the channel and having an end nearby the injection port with a seal thereon that has an orifice therein, a fluid passageway in the partition which allows the liquid to flow from the chamber into the tubular element, a plunger seated within the tubular element having one end that extends through the opening and another end in the tubular element to which is attached a resilient seal, said resilient seal fitting snug against the tubular element to grip said tubular element and, in response to movement of the plunger, to move the tubular element between a first position where said seal with the orifice therein seals the injection port as the plunger is moved towards said injection port and moves the tubular element into a position which blocks the passageway to prevent liquid in the chamber from passing into the tubular element, said plunger as it is moved towards the ejection port forcing any liquid in the tubular element through the orifice and out the injection port, and a second position where said seal with the orifice therein is moved to a retracted position away from the injection port to move the tubular element into a position which unblocks the passageway to allow liquid in the chamber to flow from the chamber through the passageway and through the orifice into the tubular member.

10. The medical syringe of claim 9 where the chamber at least partially surrounds the channel.

11. A method of giving an injection of an anesthetic into the body of a patient, including the steps of (a) providing a syringe with a reservoir that contains the anesthetic and a delivery channel which receives a plunger which when moved in one direction places the channel in communication with the reservoir and in another direction discontinues the communication and ejects anesthetic from the channel, and (b) using the syringe to initially introduce a first dosage of the anesthetic from the channel into the body of the patient, and (c) introducing a second dosage of the anesthetic by moving the plunger in the one direction to place the reservoir into communication with the channel and refill the channel with anesthetic and then moving the plunger in the other direction to discontinue the communication and eject the second dosage of anesthetic from the channel.

12. The method of claim 11 where only one hand is used to manipulate the syringe.

* * * * *